Figure 1:
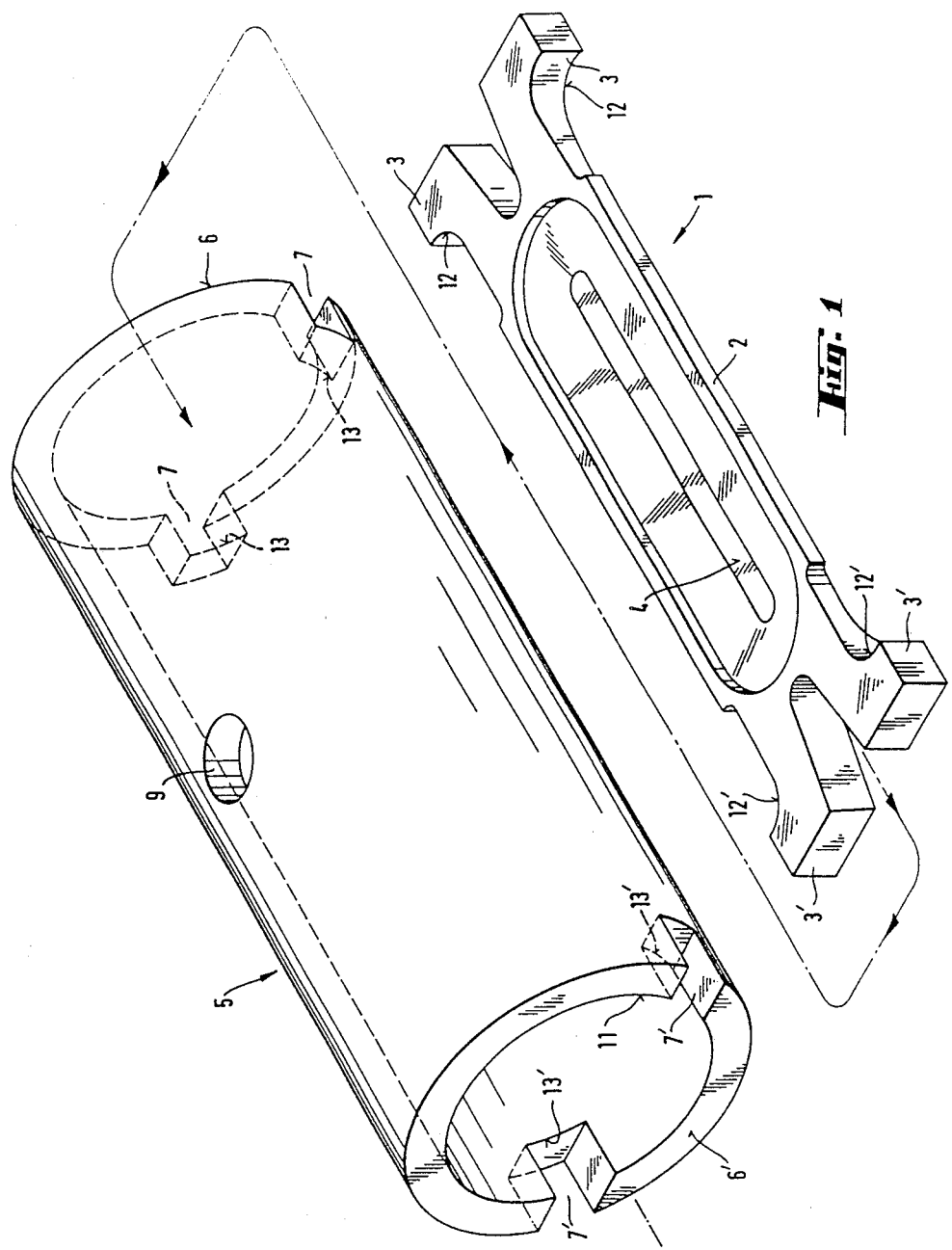

United States Patent [19]
Hütsch et al.

[11] Patent Number: 4,971,438
[45] Date of Patent: Nov. 20, 1990

[54] GRAPHITE TUBE FURNACE WITH SPECIMEN SUPPORT FOR ATOMIC ABSORPTION SPECTROSCOPY

[75] Inventors: Bruno Hütsch; Bernd Schmidt, both of Bonn, Fed. Rep. of Germany

[73] Assignee: Ringsdorff-Werke GmbH, Bonn, Fed. Rep. of Germany

[21] Appl. No.: 319,136

[22] Filed: Mar. 3, 1989

[30] Foreign Application Priority Data

Mar. 9, 1988 [DE] Fed. Rep. of Germany ....... 8803144

[51] Int. Cl.$^5$ .......................................... G01N 21/74
[52] U.S. Cl. .................................................. 356/312
[58] Field of Search .............................. 356/312, 244

[56] References Cited
U.S. PATENT DOCUMENTS
4,826,318 5/1989 Guenther et al. ................... 356/312

OTHER PUBLICATIONS

Falk et al., "Spatially and Temporally Resolved Temperature Profiles in Graphite Furnaces", Fresenius Z Anal. Chem. (1986) 323: pp. 748-753.

Primary Examiner—Vincent P. McGraw
Attorney, Agent, or Firm—Herbert L. Lerner; Laurence A. Greenberg

[57] ABSTRACT

A graphite tube furnace and a specimen support are provided for atomic absorption spectroscopy. The graphite tube furnace has end surfaces with slots. The specimen support has an intermediate or middle section with a recess for receiving a specimen and end sections which are wider than the middle section. Upon insertion in the graphite tube furnace, the specimen support is fixed with the wider end sections in the slots in the end faces and the intermediate section is held at a constant distance from the wall of the tube furnace. As a result, current conduction and heat flow between tube furnace and the specimen support are very small.

5 Claims, 1 Drawing Sheet

GRAPHITE TUBE FURNACE WITH SPECIMEN SUPPORT FOR ATOMIC ABSORPTION SPECTROSCOPY

SPECIFICATION

The invention relates to a graphite tube furnace with a specimen support for atomic absorption spectroscopy.

The first apparatus proposed by L'vov for atomic absorption spectroscopic analyses contained a graphite tube furnace in which the specimen was heated to a predetermined temperature, and then introduced into a graphite crucible or sample support which could be heated independently of the tube furnace. Vaporization and atomization of the specimen substance and the measurement of the absorption takes place in this apparatus under reproducible defined conditions so that variation in the measured values is comparatively small. However, it requires great expense to combine the apparatus and measuring process and as a consequence various simplifications have therefore been proposed, e.g. the furnace according to Massmann. With all of the modifications of the apparatus, the specimen support does not have its own resistance heating circuit so that the specimen support and the specimen are heated essentially by radiation after introduction into the graphite tube furnace In the pulse-like heating up phase, it is not possible to avoid a temperature difference between the specimen support and the shell or wall of the graphite tube furnace which is harder to reproduce and which is capable of correspondingly influencing the precision and sensitivity of the analysis.

H. Falk and A. Glismann noted that the temperature difference and the rate of heating of the specimen support at a constant heating rate for the graphite tube furnace are influenced essentially by electrical contacts between the tube shell or wall and specimen support, since a part of the furnace current flows through the mostly plate shaped specimen support lying on the furnace wall (Fresenius Z. Anal. Chem. (1986) 323, pages 748–753). The effect of different temperature differences and heating rates, e.g. in the determination of small contents of lead in blood, have been investigated by I. L. Shuttler and H T Delves (Journal of Analytical Atomic Spectroscopy (1987) Vol. 2, page 171, et seq.). With standard test supports, the spread of measured values was so great that the analysis method was not suitable for this determination. Above all, there were significant differences in the time lag of the signal and of the integral absorption which apparently go back to the differences in the rates of heating of the specimen According to the authors, the usual specimen supports are heated not only by irradiation but also by thermal conduction and joulean effect. In order to solve the problem, there has been proposed the development of specimen supports which are heated exclusively by irradiation and can be kept in a reproducible position in the tubular graphite furnace A specimen support which has a smaller contact surface with the wall or shell of the tubular graphite furnace than the square-shaped standard specimen supports is the "pin platform"(loc. cit). Such a specimen support touches pin-like supports on the wall surface of the furnace in order to reduce the contact area. However, that structure has a few disadvantages which are counter to general use. The establishment of the position of the specimen support in the graphite tube furnace is not mandatory, so that its precise position in the tube furnace is dependent on the skill of the service personnel; the heating of the support by joulean heating is not completely excluded; and finally the pin-like supports essentially limit the choice of the substance for the specimen support. Specimen supports provided with pins may only be produced from special types of graphite, e.g. from vitreous carbon which is difficult to produce and is not producible in the purity which other types of graphite have. As a rule, only supports with wider band-like rests which have greater contact surfaces with the wall of the tubular graphite furnace and a correspondingly greater current flow through the support, may be produced from the purest graphite used for the production of specimen supports, due to its smaller strength.

It is accordingly an object of the invention to provide a graphite tube furnace with a specimen support for atomic absorption spectroscopy, which overcomes the hereinaforementioned disadvantages of the heretofore-known devices of this general type.

With the foregoing and other objects in view there is provided, in accordance with the invention, an assembly for use in Atomic absorption spectroscopy, comprising a graphite tube furnace having an inner wall surface and end surfaces with slots formed in the end surfaces and a specimen support having end sections with a given width and an intermediate section between the end sections having a smaller width than the given width, the end sections being engaged in the slots for holding the specimen support at a distance from the inner wall surface.

If appropriate, in accordance with an other feature of the invention, the furnace has a longitudinal axis, and the slots have rectangular or trapezoidal cross-sections and extend essentially parallel to the longitudinal axis.

In accordance with a further feature of the invention, the intermediate section is flat and rectangular and has at least one recess formed therein for receiving a specimen. The specimen support is spatially fixed as a result of the suspension in the slots and is kept at a distance from the wall of the tube furnace so that current conduction and heat flow between the tube furnace and the specimen support are very low. As a result of the suspension, the position of the specimen support in the tube furnace is established clearly and reproducibly. Furthermore, less skilled service personnel can exchange the specimen supports without the use of special tools.

In accordance with a concomitant feature of the invention, the specimen support is formed of electrographite and has a thin pyrographite surface coating.

However, the tube furnace and the specimen support may be formed of any desired type of graphite, such as electrographite, pyrographite or vitreous carbon. Preferably the support is produced from the purest graphite which is obtained from electrographite, is easy to work and has the required purity. The support can be surface coated in known manner with a thin pyrographite layer as mentioned above, or it can be profiled, mainly to control the wettability by the substance to be analyzed.

The specimen support is pushed into the cold or preheated graphite tube furnace and heated almost exclusively by thermal radiation so that, in particular, the temperature increase in the sample, and the evaporation and atomization of the substance to be analyzed is adjusted and controlled by the electric loading of the graphite tube furnace. With a preset analysis program, the variation of the time lag for the signals is very small and the reproducibility of the measurement is extraordinarily good. The specimen supports are formed of the types of graphite or carbon which correspond best of all to the analysis conditions concerned and have, for example, a specific porosity, hardness or purity. There is no limitation to the use of only vitreous carbon as with the known "pin platform".

In addition to the above-described advantages, experiments with the apparatus have shown another improvement which occurs with supports with the Zeeman background corrector. The overall apparatus is brought into a strong magnetic field with the oscillations occurring so strongly in parts, that the specimen support is moved out of the tubular graphite furnace. Specimen supports which are held as a result of the connection thereof do not vary their position relative to the graphite tube furnace and are also suitable for this analysis process.

Other features which are considered as characteristic for the invention are set forth in the appended claims.

Although the invention is illustrated and described herein as embodied in a graphite tube furnace with a specimen support for atomic absorption spectroscopy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing. The drawing is a diagrammatic, exploded perspective view of a specimen support and a tubular graphite furnace associated therewith, which give a better understanding of the invention and the operation thereof by way of example only.

Referring now in detail to the single figure of the drawing, there is seen a specimen support 1 containing an intermediate section 2 and end sections 3 and 3' which have a greater width than the intermediate section. A trough shaped recess 4 is incorporated for receiving the specimen. The specimen support 1 is pushed into a graphite tube furnace 5 which has a hole 9 formed therein, in such a way that the support 1 is in the plane of a main section. The support is then lowered so that the end sections 3, 3' engage in groove shaped slots 7, 7' which are formed in end or front surfaces 6 of the tube furnace 5. Surfaces 12, 12' of the end sections 3, 3'lie on edges 13, 13' and the intermediate section 2 is held at a distance from an inner wall surface 11 of the furnace 5. The foregoing is a description corresponding in substance to German Application G No. 88 03 144.6, dated Mar. 9, 1988, the International priority of which is being claimed for the instant application, and which is hereby made part of this application. Any material discrepancies between the foregoing specification and the aforementioned corresponding German application are to be resolved in favor of the latter.

We claim:

1. Assembly for use in atomic absorption spectroscopy, comprising a graphite tube furnace having an inner wall surface and end surfaces with slots formed in said end surfaces; and a specimen support having end sections with a given width and an intermediate section between said end sections having a smaller width than said given width, said end sections being engaged in said slots for holding said specimen support at a distance from said inner wall surface and preventing said specimen support from moving out of said furnace.

2. Assembly according to claim 1, wherein said furnace has a longitudinal axis, and said slots have rectangular crosssections and extend parallel to said longitudinal axis.

3. Assembly according to claim 1, wherein said furnace has a longitudinal axis, and said slots have trapezoidal crosssections and extend parallel to said longitudinal axis.

4. Assembly according to claim 1, wherein said intermediate section is flat and has at least one recess formed therein for receiving a specimen.

5. Assembly according to claim 1, wherein said specimen support is formed of electrographite and has a thin pyrographite surface coating.

* * * * *